United States Patent
Fogarty et al.

(10) Patent No.: US 6,699,259 B2
(45) Date of Patent: *Mar. 2, 2004

(54) MINIMALLY INVASIVE DIRECT CARDIAC MASSAGE DEVICE AND METHOD

(75) Inventors: Thomas J. Fogarty, Portola Valley, CA (US); Timothy James Ryan, Portola Valley, CA (US)

(73) Assignee: Revivant Corporation, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/337,694

(22) Filed: Jan. 6, 2003

(65) Prior Publication Data

US 2003/0105481 A1 Jun. 5, 2003

Related U.S. Application Data

(63) Continuation of application No. 09/567,844, filed on May 9, 2000, now Pat. No. 6,503,265, which is a continuation of application No. 08/691,042, filed on Aug. 1, 1996, now Pat. No. 6,059,750.

(51) Int. Cl.[7] .................... A61H 31/00; A61M 29/04
(52) U.S. Cl. .................. 606/192; 606/198; 601/153; 600/207; 600/18
(58) Field of Search .................. 601/153, 151, 601/41, 44, 106; 600/18, 207; 604/96.01, 98.01, 192; 606/198, 192

(56) References Cited

U.S. PATENT DOCUMENTS

| 4,048,990 A | 9/1977 | Goetz ........................ 128/64 |
| 4,570,615 A | 2/1986 | Barkalow .................. 128/28 |
| 4,710,181 A | * 12/1987 | Fuqua ...................... 604/514 |
| 5,385,528 A | 1/1995 | Wilk ........................ 600/18 |
| 5,439,476 A | 8/1995 | Frantzides .............. 606/192 |
| 5,466,221 A | 11/1995 | Zadini et al. ............ 604/96 |
| 5,484,391 A | 1/1996 | Buckman, Jr. et al. ..... 601/135 |
| 5,496,345 A | * 3/1996 | Kieturakis et al. ........ 606/192 |
| 5,607,441 A | * 3/1997 | Sierocuk et al. .......... 606/190 |
| 5,607,443 A | * 3/1997 | Kieturakis et al. ........ 606/192 |
| 5,836,961 A | * 11/1998 | Kieturakis et al. ........ 606/190 |
| 5,868,707 A | * 2/1999 | Williams et al. .......... 604/103 |
| 6,036,640 A | * 3/2000 | Corace et al. ............. 600/207 |

OTHER PUBLICATIONS

Buckman, et al., Direct Cardiac Massage Without Major Thoracotomy, 29 Resuscitation 237 (1995).

Taylor, et al., External Cardiac Compression, A Randomized Comparison Of Mechanical and Manual Techniques, 240 JAMA 644 (Aug. 1978).

Hightower, et al., Decay In Quality Of Chest Compressions Over Time, 26 Ann. Emerg. Med. 300 (Sep. 1995).

* cited by examiner

Primary Examiner—Danton D. DeMille
(74) Attorney, Agent, or Firm—K. David Crockett, Esq.; Crockett & Crockett

(57) ABSTRACT

A minimally invasive device for performing direct cardiac massage including an inflatable bladder mounted on a rigid inflation tube. The rigid inflation tube is used to push the bladder into the sternocostal space through an incision in the upper abdomen just below the xiphoid process. A tear-away insertion sleeve is provided over the balloon, so that the device may easily be inserted in to the body. The insertion sleeve includes various features that assist in placement of the device and removal of the sleeve. After insertion into the sternocostal space and removal of the insertion sleeve, the bladder is repeatedly inflated and deflated to massage the heart and provide blood flow.

8 Claims, 9 Drawing Sheets

MINIMALLY INVASIVE DIRECT CARDIAC MASSAGE DEVICE AND METHOD

This application is a continuation of U.S. application Ser. No. 09/567,844 filed May 9, 2000, now U.S. Pat. No. 6,503,265, which is a continuation of U.S. application Ser. No. 08/691,042 filed Aug. 1, 1996, now U.S. Pat. No. 6,059,750.

FIELD OF THE INVENTION

This invention relates to cardiopulmonary resuscitation and cardiac massage.

BACKGROUND OF THE INVENTION

Cardiopulmonary resuscitation (CPR) is a well known and valuable method of first aid. CPR is used to resuscitate people who have suffered from cardiac arrest after heart attack, electric shock, chest injury and many other causes. During cardiac arrest, the heart stops pumping blood, and a person suffering cardiac arrest will soon suffer brain damage from lack of blood supply to the brain. Thus, CPR requires repetitive chest compression to squeeze the heart and the thoracic cavity to pump blood through the body. Very often, the victim is not breathing, and mouth to mouth artificial respiration or a bag valve mask is used to supply air to the lungs while the chest compression pumps blood through the body.

It has been widely noted that CPR and chest compression can save cardiac arrest victims, especially when applied immediately after cardiac arrest. Chest compression requires that the person providing chest compression repetitively push down on the sternum of the victim at 80–100 compressions per minute. CPR and closed chest compression can be used anywhere, wherever the cardiac arrest victim is stricken. In the field away from the hospital, it may be accomplished by ill-trained by-standers or highly trained paramedics and ambulance personnel or at the hospital where it can be accomplished by doctors and nurses.

When a first aid provider performs chest compression well, blood flow in the body is typically about 25–30% of normal blood flow. This is enough blood flow to prevent brain damage. However, when chest compression is required for long periods of time, it is difficult if not impossible to maintain adequate compression of the heart and rib cage. Even experienced paramedics cannot maintain adequate chest compression for more than a few minutes. Hightower, et al., Decay In Quality Of Chest Compressions Over Time, 26 Ann. Emerg. Med. 300 (September 1995). Thus, long periods of CPR, when required, are not often successful at sustaining or reviving the victim. At the same time, it appears that, if chest compression could be adequately maintained, cardiac arrest victims could be sustained for extended periods of time. Occasional reports of extended CPR efforts (45–90 minutes) have been reported, with the victims eventually being saved by coronary bypass surgery. See Tovar, et al., Successful Myocardial Revascularization and Neurologic Recovery, 22 Texas Heart J. 271 (1995).

Mechanical devices for closed chest compression have been proposed and used. The device shown in Barkolow, Cardiopulmonary Resuscitator Massager Pad, U.S. Pat. No. 4,570,615 (Feb. 18, 1986), the commercially available-thumper device, and other such devices, provide continuous automatic closed chest compression. However, these devices are not clinically more successful that manual chest compression. See Taylor, et al., External Cardiac Compression, A Randomized Comparison of Mechanical and Manual Techniques, 240 JAMA 644 (August 1978). Active compression decompression using a device which also lifts the chest wall after compression has been proposed. Stiel, et al., The Ontario Trial of Active Compression and Decompression Cardiopulmonary Resuscitation for In-Hospital and Prehospital Cardiac Arrest, 275 JAMA 1417 (1996) compared active compression-decompression with standard CPR, and found no significant improvement in survival or neurological outcome. A variety of other methods of increasing the effectiveness of CPR have been proposed, including abdominal binding and anti-shock pants. These techniques are intended to block blood flow to the abdomen and legs, thus directing blood flow to the brain. Again, these techniques have not proven effective in boosting the survival rate of cardiac arrest victims.

Chest compression must be accomplished vigorously if it is to be effective. Very little of the effort exerted in chest compression actually compresses the heart and large arteries of the thorax and most of the effort goes into deforming the chest and rib cage. The force needed to provide effective chest compression creates risk of other injuries. It is well known that placement of the hands over the sternum is required to avoid puncture of the heart during CPR. Numerous other injuries have been caused by chest compression. See Jones and Fletter, Complications After Cardiopulmonary Resuscitation, 12 AM. J. Emerg. Med. 687 (November 1994), which indicates that lacerations of the heart, coronary arteries, aortic aneurysm and rupture, fractured ribs, lung herniation, stomach and liver lacerations have been caused by CPR. Thus the risk of injury attendant to chest compression is high, and clearly may reduce the chances of survival of the victim vis-a-vis a resuscitation technique that could avoid those injuries. Also, chest compression will be completely ineffective for very large or obese cardiac arrest victims because the chest cannot be compressed enough to cause blood flow.

In the hospital setting, when closed chest compression is ineffective, doctors have the option of using open chest compression (also referred to as cardiac massage, open cardiac massage, open resuscitation, etc.). To accomplish open chest compression, the doctors perform a thoracotomy and pull the rib cage apart to open the chest, cut the heart out of the pericardial sac and expose the heart, and then "massage" the heart by hand (they squeeze it like a bladder pump). Mechanical devices for squeezing the heart during open chest surgery have been proposed, such as Goetz, Heart Massage Apparatus, U.S. Pat. No. 4,048,990, which provides a tulip shaped or basket-shaped bladder to surround the heart after the chest has been opened and the heart dissected from the pericardial sac. The grossly invasive thoracotomy procedure required for manual or mechanical open heart massage can only be accomplished in the hospital, and it carries its own risk of killing the cardiac arrest victim. Open chest cardiac massage is viewed as a last resort. See Blakeman, Open Cardiac Resuscitation, A Surgeons Viewpoint, 87 Postgraduate Med. 247 (January 1990). However, it has the benefit of increased blood flow compared to closed chest compressions, about 50% of normal blood flow. Bartlett, et al., Comparative Study Of Three Methods Of Resuscitation: Closed Chest, Open Chest Manual And Direct Mechanical Ventricular Assistance, 13 Ann. Emerg. Med. 773 (1984).

Direct cardiac massage can be accomplished without open heart surgery. Buckman, et al., Direct Cardiac Massage Without Major Thoracotomy, 29 Resuscitation 237 (1995) shows a cardiac compression device which has a small plate mounted on a handle, like a potato masher or a toilet plunger.

The device is inserted through the chest wall, through an incision between the ribs which is 7.5 cm long. The device is placed so that the small plate is in contact with the left ventricle, then it is manually pushed against the heart to squeeze the heart. In both open cardiac massage and Buckman's minimally invasive direct cardiac massage, blood flow is accomplished by mechanically squeezing the heart so that it acts like a bladder pump.

SUMMARY OF THE INVENTION

The cardiac pumping device and method presented below allows for direct cardiac massage in a procedure that can easily be accomplished by emergency medical personnel, paramedics, doctors and nurses, and probably by anyone trained in first aid. The substernal cardiac pump includes an inflatable balloon mounted on a rigid tube. The tube has inflation ports opening into the balloon, and a long handle section which is attached to an air pump. The air pump is preferably a positive placement dual action pump, so that it pumps air into the balloon on the pumping stroke and sucks air out of the balloon during the reset stroke. Thus the balloon can be repeatedly inflated and deflated. When inflated, the balloon has a shape which accommodates the heart and squeezes the heart.

To use the cardiac pump on a cardiac arrest victim, the medic makes a small incision (two or three centimeters is sufficient) just below the sternum. The incision is shallow, just enough to puncture the skin and any fat beneath the skin. After making this initial incision, the medic sticks his finger through the incision, slides his finger along the undersurface of the sternum and pushes a hole up through the diaphragm of the victim. This creates a channel into the thorax of the victim. This is all the preparation that is needed for insertion of the cardiac pump. With the channel easily made, the medic pushes the balloon through the channel, into the thorax, and in place over the heart. The medic then operates the air pump to inflate and deflate the balloon repeatedly. Every time the balloon is inflated, it expands between the sternum and the heart, and thus squeezes the heart.

Various additional features are added to make the cardiac pump easy to use. The hand pump may be hooked up to a small electric motor, powered by battery, standard household current, or through an automobile cigarette lighter or other mobile power sources carried by ambulances. A variety of other air pump mechanisms can be used. The cardiac pump can be provided with over-pressure relief valves to limit the pressure within the balloon. The cardiac pump can be provided with a low pressure warning system to indicate rupture of the balloon or a leak in the inflation pathway. The size of balloon inflation can be adjusted up or down in response to feedback from information gathered from measurement of the air exhaled by the victim.

The cardiac pump makes it easy to provide adequate heart compression for extended periods of time, without loss of effectiveness due to fatigue of medics. The placement of the cardiac pump is simply accomplished, and direct cardiac massage is accomplished without thoracotomy or large incision. Actual compression of the heart is limited by the size of the balloon and/or the pressure limits of the inflation system.

DETAILED DESCRIPTION OF THE INVENTION

Figure 1:
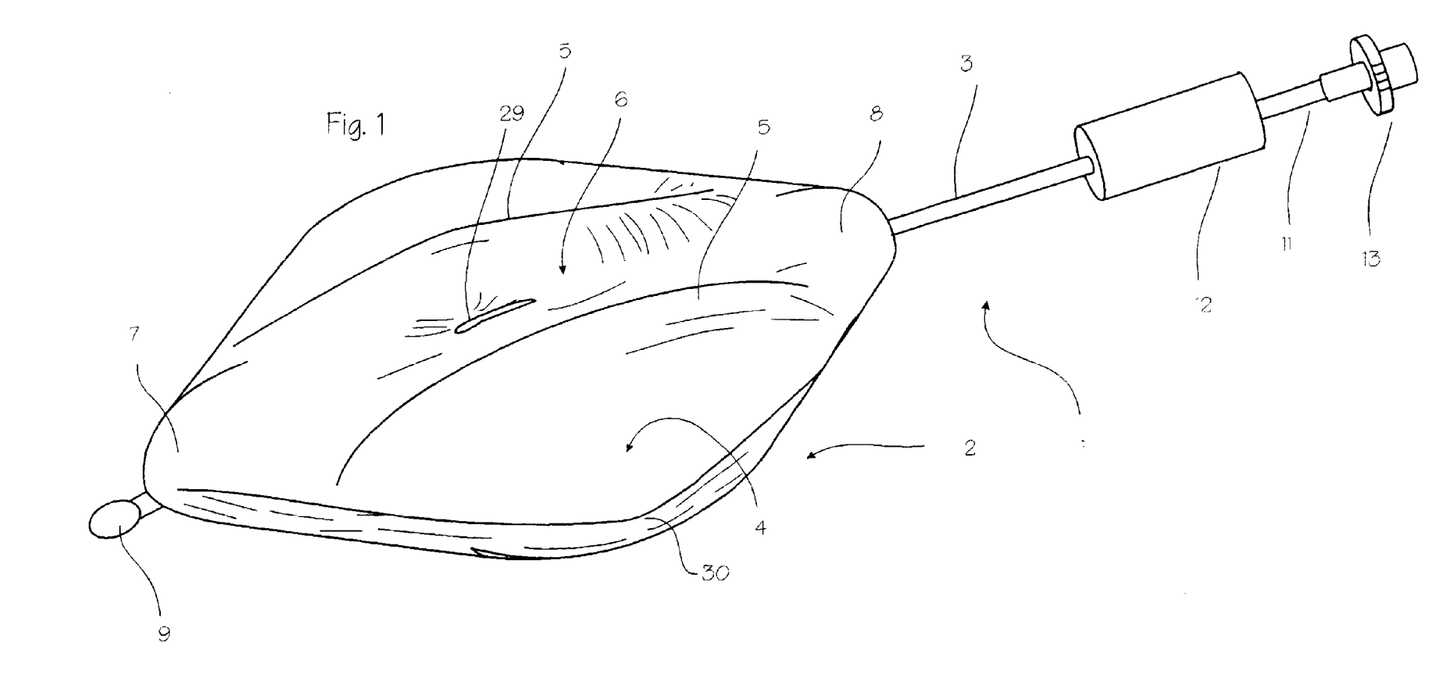
FIGS. 1 and 2 show the cardiac pump.

FIG. 1 shows the cardiac pump 1. The balloon 2 is mounted on the rigid inflation tube 3. The balloon has a rounded diamond shape, or a manta ray shape when viewed from above. The posterior surface 4 of the balloon has a railed shape when inflated, with rails 5 defining a heart receiving recess 6 in the central portion of the posterior surface. The balloon is sealed to the tube at the distal end 7 of the balloon and the proximal end 8 of the balloon. The distal end of the tube may extend a short distance from the distal end of the balloon, and is fitted with an atraumatic tip 9 which can help dissect tissue when the device is pushed into the chest cavity. The portion of the rigid tube inside the balloon has inflation outlets 10, seen in FIG. 5, which allow inflation fluid to pass into and out of the balloon. Referring again to FIG. 1, near the proximal end 11 of the rigid tube, a handle 12 is fitted to the tube and a fluid tight connector 13 such as a typical Luer fitting, quick disconnect or other type fitting is fitted to the tube in order to provide a fluid path from the air pump, through the rigid tube and into the balloon.

Figure 2:
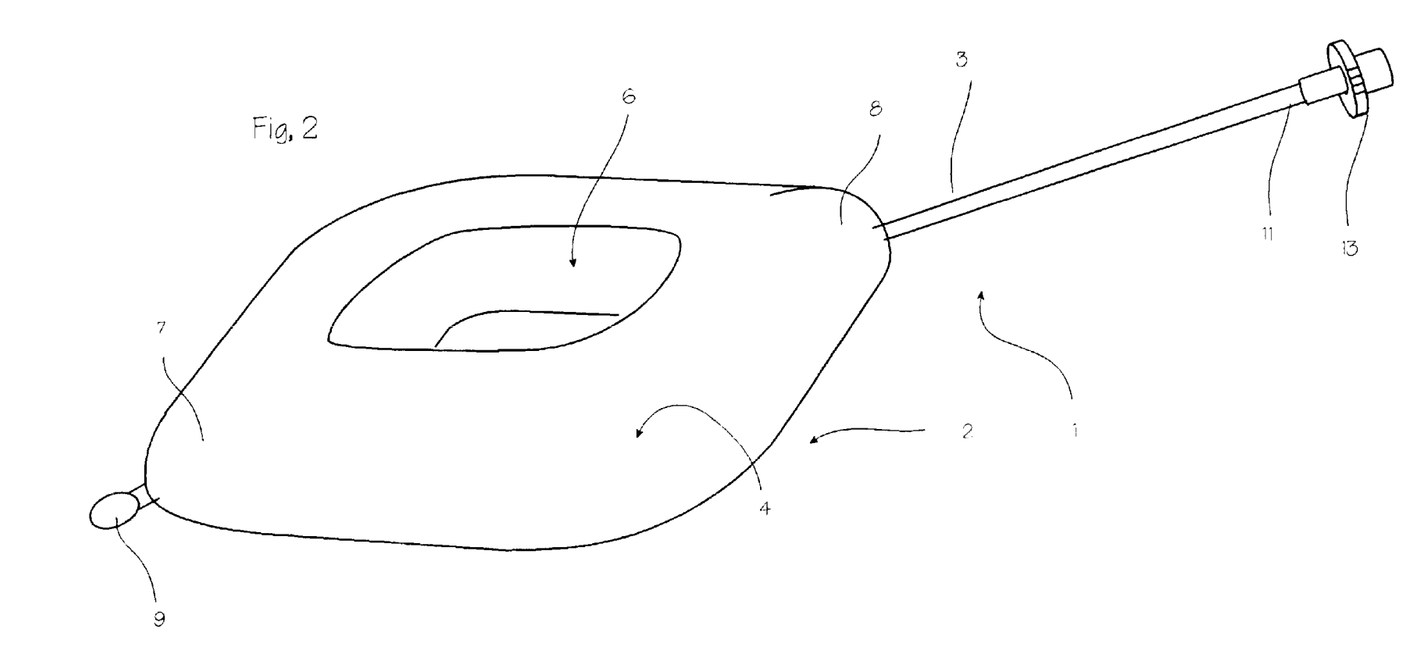

FIG. 2 shows another shape for the cardiac pump. The balloon has an annular bulge around its perimeter which defines a recess 6 in the center or the posterior surface 4 which will fit over the heart and rest on the rounded anterior surface of the heart. The overall shape of the posterior surface 4 in both FIGS. 1 and 2 is gently cupped to receive the heart, and maybe described as palmate or palm shaped, such that it conforms to the gently curved anterior surface of the heart. This shape permits placement of the balloon over the heart and effective inflation to compress the heart, while also assisting in maintaining the balloon in place over the heart. A slightly convex shape on the posterior surface is also useful to compression of the heart. Merely spherical or bulb shaped balloons may also be used.

Figures 3, 4:
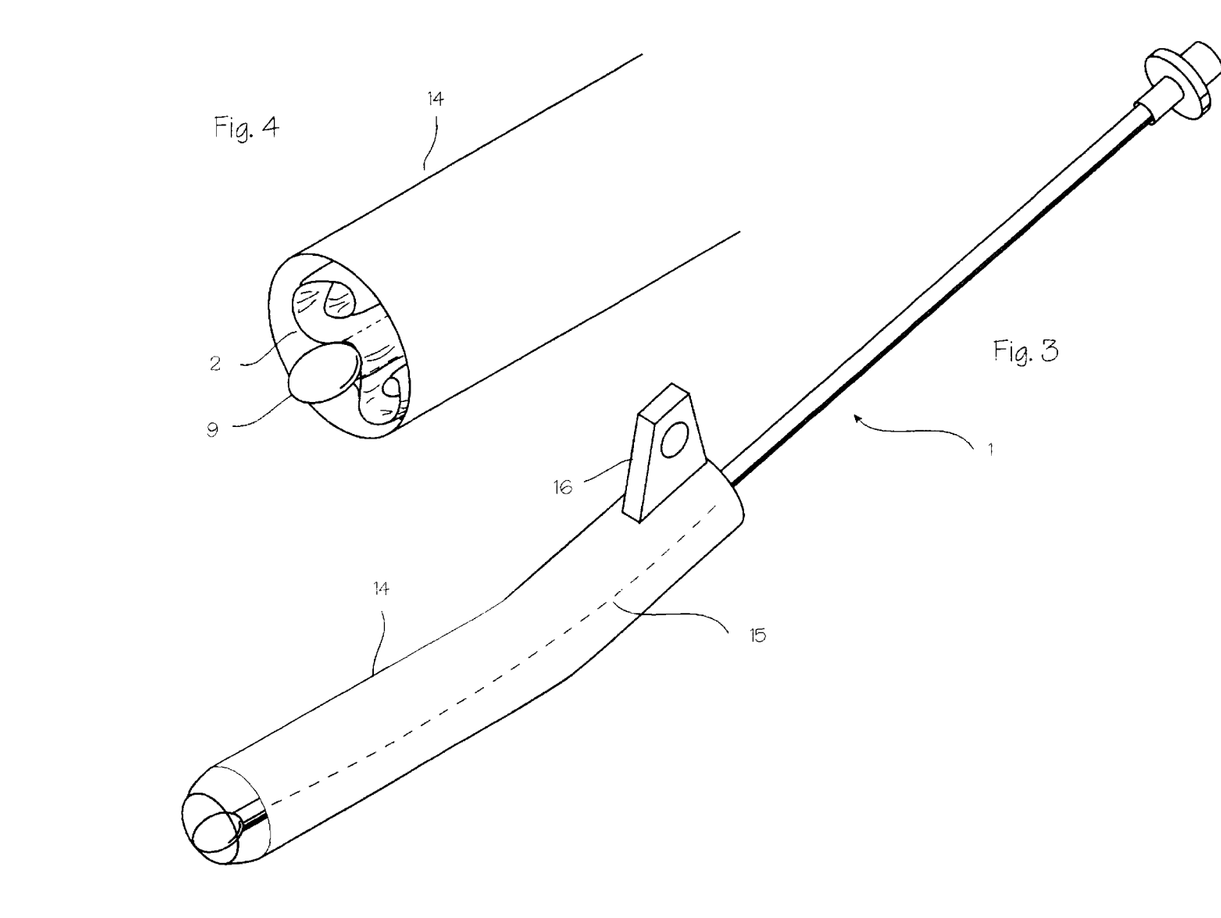
FIGS. 3 and 4 show the cardiac pump inserted inside an introducer sheath.

FIG. 3 shows an optional plastic introducer sleeve 14 with a rounded distal tip which may be used to facilitate insertion of the balloon into the chest. Each lateral corner 20 (indicated in FIG. 6) of the balloon is rolled toward the center of the balloon, and the device is slipped into the introducer sleeve. The sleeve is a tear away sheath and has scored line 15 on the side to allow the sleeve to be removed from the device by tearing the sleeve along the scored line.

The scored line is provided along the side of the device so that side-ways pull is necessary, thus avoiding the need for any upward force which could cause the tip to be forced downward into the heart, a concern that will become apparent from the description of use provided below. The pull tab 16 also serves as a distinguishing shape indicating the front of the device, and serves as a physical stop which prevents incorrect insertion of the device (i.e. insertion with the anterior surface of the balloon facing the heart). FIG. 4 shows the detail of the balloon 2 folded within the sleeve as viewed from the distal end of the device.

Figure 5:
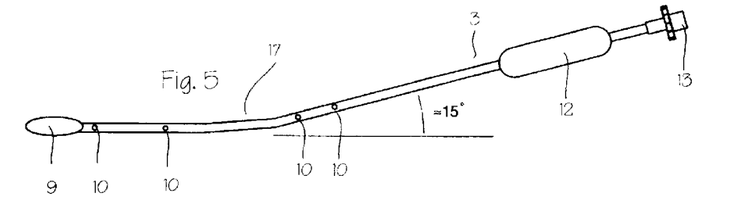
FIG. 5 is a detail of the inflation tube.

FIG. 5 shows the preferred structure of the rigid tube 3. The tube has a bend 17 of approximately 15 degrees near the midpoint of the balloon 2. This bend helps orient the tube so that the tip is urged upward into contact with the sternum rather than into softer tissue in the thoracic cavity, while allowing the device to be pushed upward into the thoracic cavity at a natural angle. The bend may be any convenient angle which facilitates insertion. The inflation ports 10 are shown along the distal portion of the rigid tube, corresponding to that part of the tube surrounded by the balloon. The atraumatic olive tip 9 prevents unnecessary tearing while allowing for any needed dissection of tissue away from the sternum to permit passage of the balloon device into the substernal space above the heart. The proximal section of the tube 11 is provided with any type of quick disconnect fitting 13 typically used for medical devices. The handle 12 shown in FIGS. 1 and 5 may be made in any comfortable size, or omitted altogether. The top or anterior surface of the device, which is the preferred orientation for insertion and use, may be marked on the tube or handle in any suitable manner, either with printed instructions, color coding, texture or shape. The anterior side of the tube may be fitted with large fin which does not permit incorrect insertion. Also, the length of the inserted portion of the balloon device can be indicated by markings, such as ruler markings on the rigid tube, in order to provide medics with an indication of how far the device is inserted, thus ensuring its proper placement in position over the heart. The rigid tube may be made of any material sufficiently rigid to permit insertion into the thoracic cavity through the prepared channel. Stainless steel, nitinol and other metals, hard plastics, graphite composites and numerous other materials may be used.

Figures 6A, 6B:
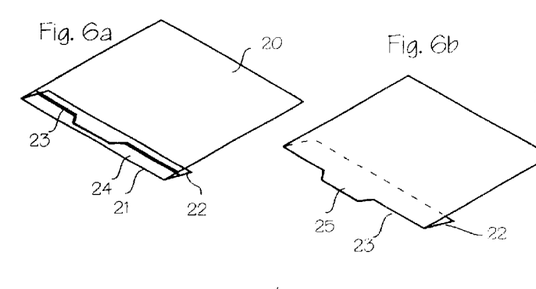
FIGS. 6a, 6b, 6c and 7 show details of the balloon
Figure 6C:
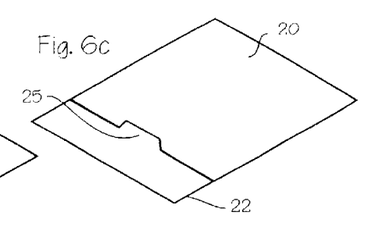
Figure 7:
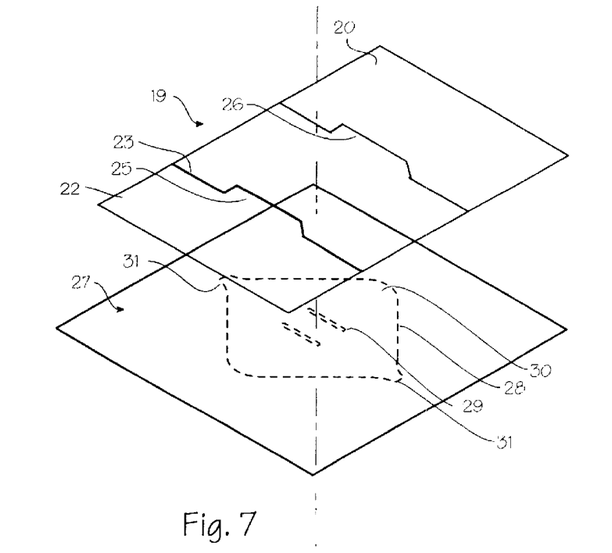

The balloon 2 as shown in FIG. 1 is fabricated of pieces as shown in FIGS. 6a, 6b, 6c and 7. The balloon top piece 19 shown in FIG. 7 is made of a single piece of plastic. The series of steps used to create pleats which, when filled with air comprise the rails 5 of the balloon shown in FIG. 1, is illustrated in FIGS. 6a, 6b and 6c. In FIG. 6a, the plastic sheet 20 is folded along the crease 21 and the folded portion 22 is heat sealed together with the major portion along heat seal line 23. The waste area 24 is trimmed away and the top piece appears as illustrated in FIG. 6b with pleat 25 formed. The top piece, when unfolded and laid flat, appears as shown in FIG. 6c, with the pleat 25 extending upwardly from the sheet. The process is repeated on the other side of the sheet 20 to form a second pleat 26. When the top piece is complete, as illustrated in FIG. 7, it is heat sealed to the balloon bottom piece 27 along generally diamond shaped outline 28 and sealing darts 29 shown in dotted lines. The overall diamond shape has rounded corners 30 on the lateral corners of the balloon and extended corners 31 on the distal and proximal ends of the balloon. These extended corners are used to seal the balloon to the insertion tube.

Figure 8:
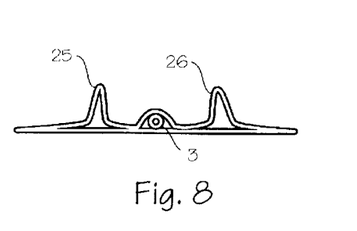
FIGS. 8 and 9 show cross sections of the balloon.
Figure 9:
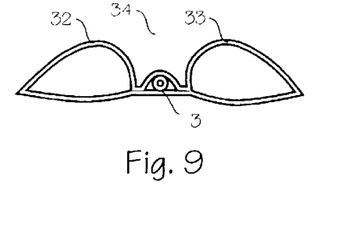

The cross section of the balloon in its deflated state is shown in FIG. 8, while the cross section of the balloon when inflated is shown in FIG. 9. When inflated, the pleats 25 and 26 form inflated rails 32 and 33 extending parallel to the center axis of the balloon, with a recess 34 between the rails, so that the balloon, when properly place over the heart, will curve around the surface of the heart and partially enclose the heart. The rigid tube 3 fits between the sealing darts 30.

Figure 10:
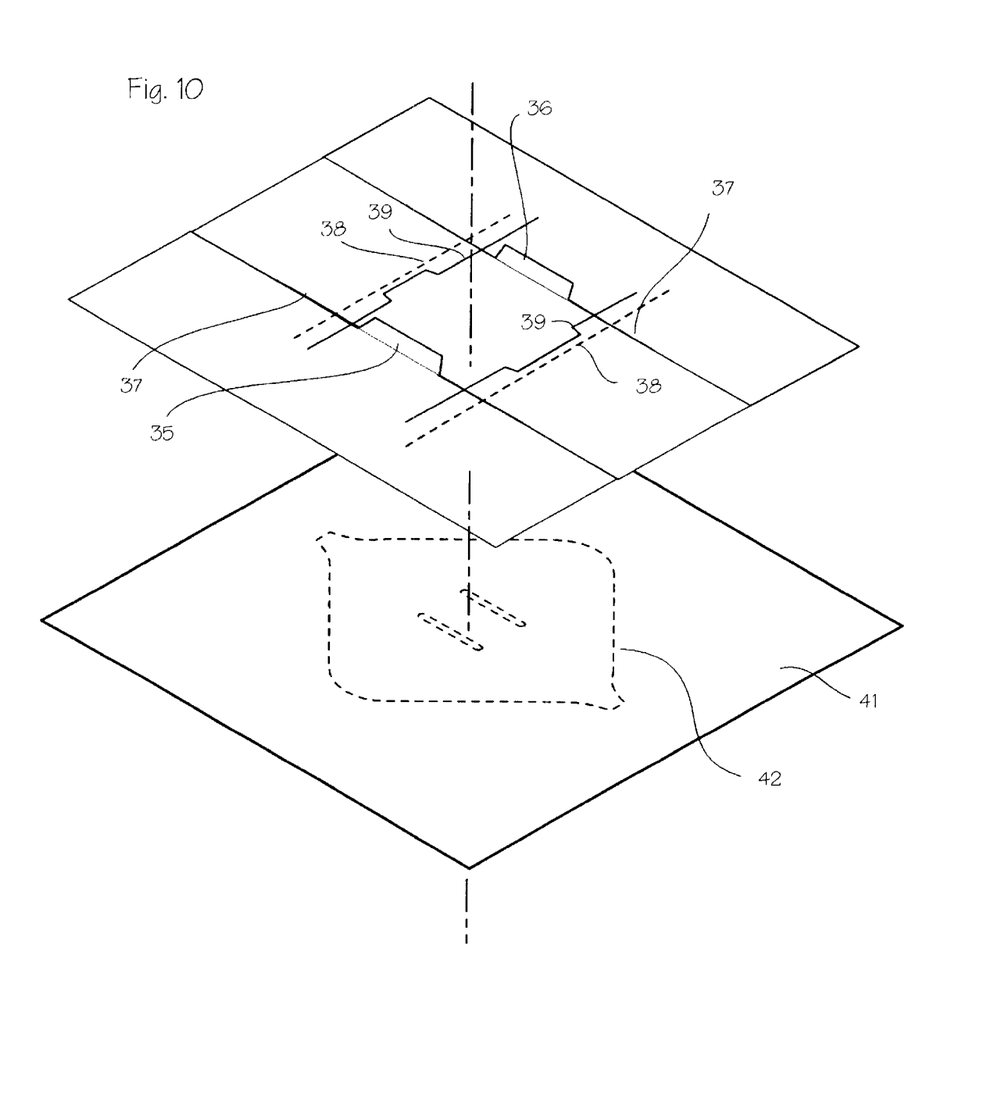
FIG. 10 shows an exploded view of the pieces used to fabricate the balloon of FIG. 2.

The balloon of FIG. 2 may be formed of pieces as shown in FIG. 10. The posterior surface 4 is made from a single sheet of plastic 20 in the same manner as that described above in reference to FIGS. 6a, 6b, 6c and 7 for the posterior surface of the balloon of FIG. 1. The sheet 20 is provided with pleats 35 and 36, which are formed in the same manner as illustrated in FIGS. 6a, 6b, and 6c. Heat seal lines 37 have already been heat sealed together. Excess material has been trimmed from pleats 35 and 36. Perpendicular pleats are then formed by folding the sheet along dotted lines 38 and heat sealing the seam together along heat seal lines 39 and trimming away excess plastic. Four pleated tabs will remain after excess plastic above the heat seal lines is removed. The bottom piece 41 is aligned with the top piece and the two are sealed together around outline 42 and the diamond shaped balloon with a ring of pleats on the posterior surface is formed. When inflated, this balloon will appear as illustrated in FIG. 2.

The balloon pieces are made of plastic such as polyurethane, polypropylene or polyethylene. The pieces are joined by heat sealing or adhesive. Balloon wall thickness of a few mils (4 mils) is sufficient to ensure adequate strength of the balloon. The balloon may also be made of elastometric materials, rubber, thermoplastic elastomers, latex, etc., and other non-elastomeric materials such as PTFE, canvas, woven polyester, nylon or sailcloth, etc. After joining the pieces together, the extended corners 21 form sleeves. The rigid tube is slipped into the balloon through the sleeves, and the sleeves are sealed to the tube to form an airtight bladder mounted on the rigid tube. For insertion the rounded corners of the balloon may be rolled inward toward the rigid tube, as shown in FIG. 4, and covered with a tear-away sheath, an introducer sheath, or a thin walled cannula which is pulled back after the balloon is in place.

It will be appreciated that more rudimentary embodiments and more complex embodiments of the balloon will also be useful. A simple pillow shape, which may be accomplished by heat sealing two diamond shapes together, or, for a fatter balloon, may be made in accordance with the steps described but without sealing the darts 29 to create the recess 6 shown in FIGS. 1 and 2. A mere round balloon mounted on a cannula or catheter can be used to take advantage of the method presented herein while producing some beneficial level of heart compression, and very complex geometries may be envisioned to distribute inflation pressure more precisely and evenly about the heart and produce optimal levels of heart compression. It should also be appreciated that the rigid tube used for inflation may be omitted in favor of more complex insertion mechanisms. The balloon may be rolled inside the lumen of a cannula, catheter or trocar and pushed from the lumen after insertion of the cannula, catheter or trocar into the chest. Inflation and deflation may then be accomplished by a flexible tube attached to the balloon.

Figure 11:
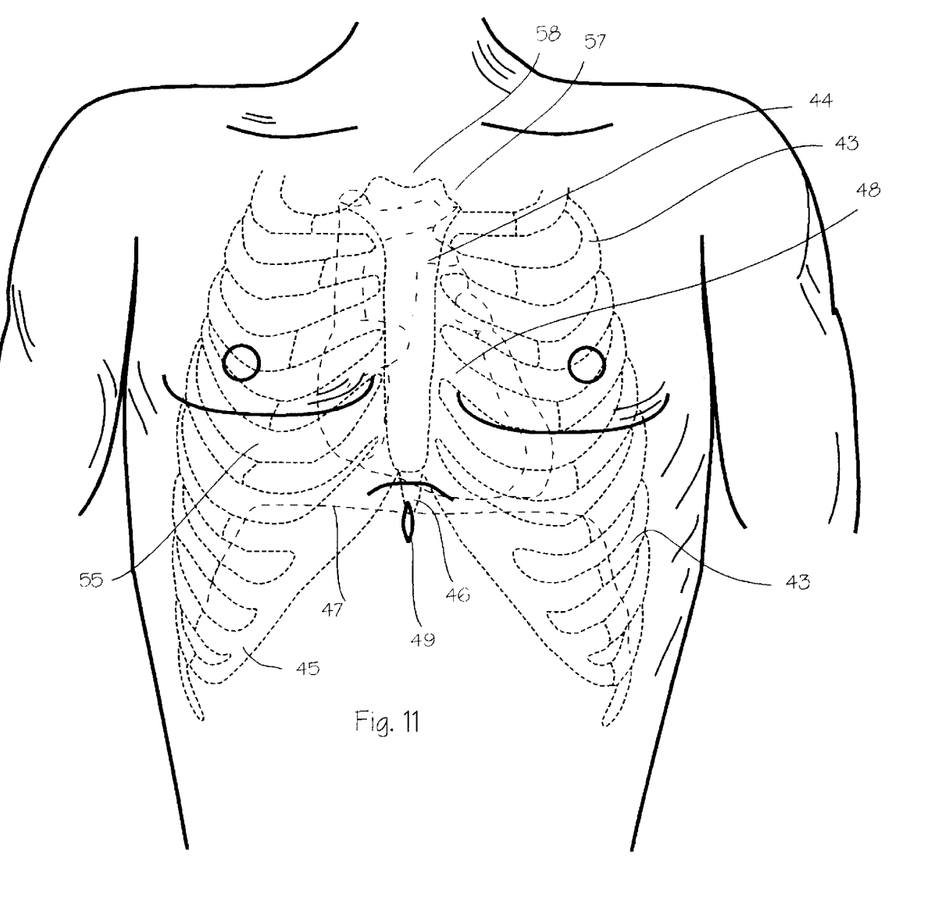
FIG. 11 shows an anterior view of a human chest and the insertion pathway for the cardiac pump.

FIG. 11 shows the insertion point of the cardiac pump. The rib cage is comprised of the ribs 43, sternum 44, the costar cartilage 45 which joins the ribs to the sternum, and the xiphoid process 46. The diaphragm 47 separates the thoracic cavity from the abdomen. The heart 48 is located in the center of the chest under the sternum, just above the diaphragm. A small vertical incision 49, just about 15 mm in length, is made just below the sternum 44 and the xiphoid process 46.

Figures 12, 13:
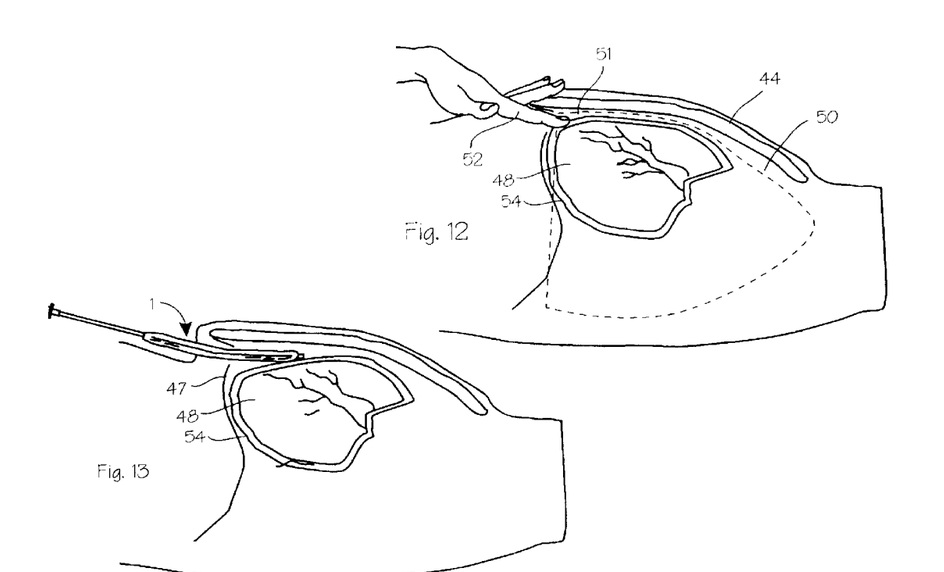
FIG. 12 shows cross section of a human chest and preparation of the insertion pathway for the cardiac pump.
FIG. 13 shows cross section of a human chest and the initial placement of the cardiac pump.

FIG. 12 shows a sagittal cross section of the human chest showing proper insertion pathway for placement of the cardiac pump into the chest of a cardiac arrest victim. The area delineated by the dotted line 50 is called the mediastinum. The heart is located in the middle mediastinum and the balloon is to be inserted into the anterior mediastinum. This space, indicated by arrow 51, is also referred to as the substernal space or the sternocostal space. The medic uses an index finger 52 to push a hole up under the sternum 44 and through the diaphragm 47 and into the anterior mediastinum or sternocostal space 51 between the sternum and the heart. A blunt dissection tool may be required, and mayo scissors may be used to help punch the hole through the diaphragm. Thus, the cardiac pump may be placed, as illustrated in FIGS. 11 and 12, without substantially altering, disrupting or cutting through the rib cage, and without need to cut or retract bone or cartilage, and incision through soft tissue is all that is required to insert the pump into the substernal space.

FIG. 13 shows a cross section of the human chest showing the placement of the cardiac pump. The tip of the cardiac pump 1 is inserted into the small incision and pushed along the channel formed by the finger, until it pushes through the hole in the diaphragm 47 and rests in the anterior mediastinum (or substernal or sternocostal) space 51 between the heart and the sternum. The 15 degree bend in the rigid tube permits easy insertion of the device while urging the distal tip upward toward the sternum and away from the heart. The ideal position for the cardiac pump is directly above the heart. Note that the heart is surrounded by the pericardial sac 54 and that the pericardial sac need not be penetrated for operation of the cardiac pump.

Figures 14, 15:
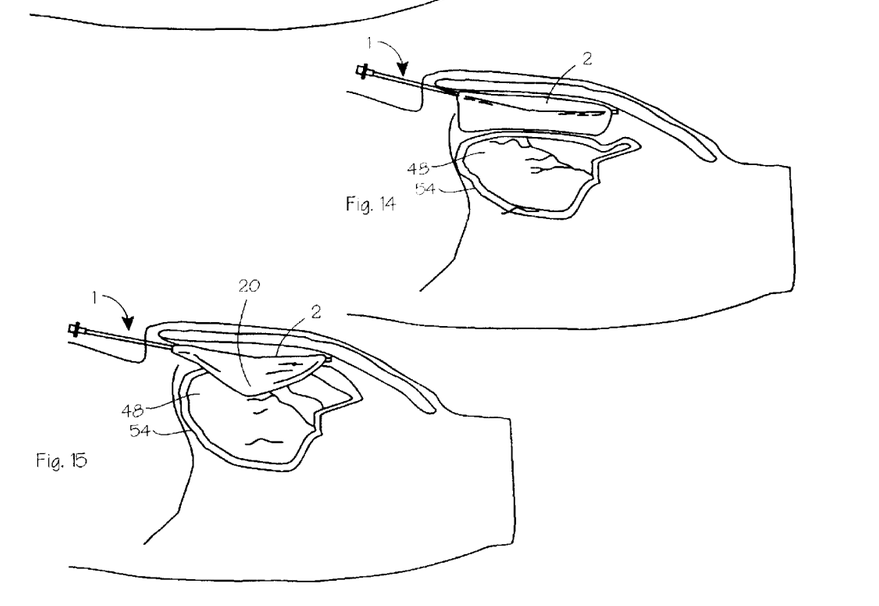
FIG. 14 is an illustration of the cardiac pump placed inside the chest of a human being and inflated to compress the heart.
FIG. 15 is an illustration of the cardiac pump deflated inside the chest to allow expansion of the heart.
Figure 16:
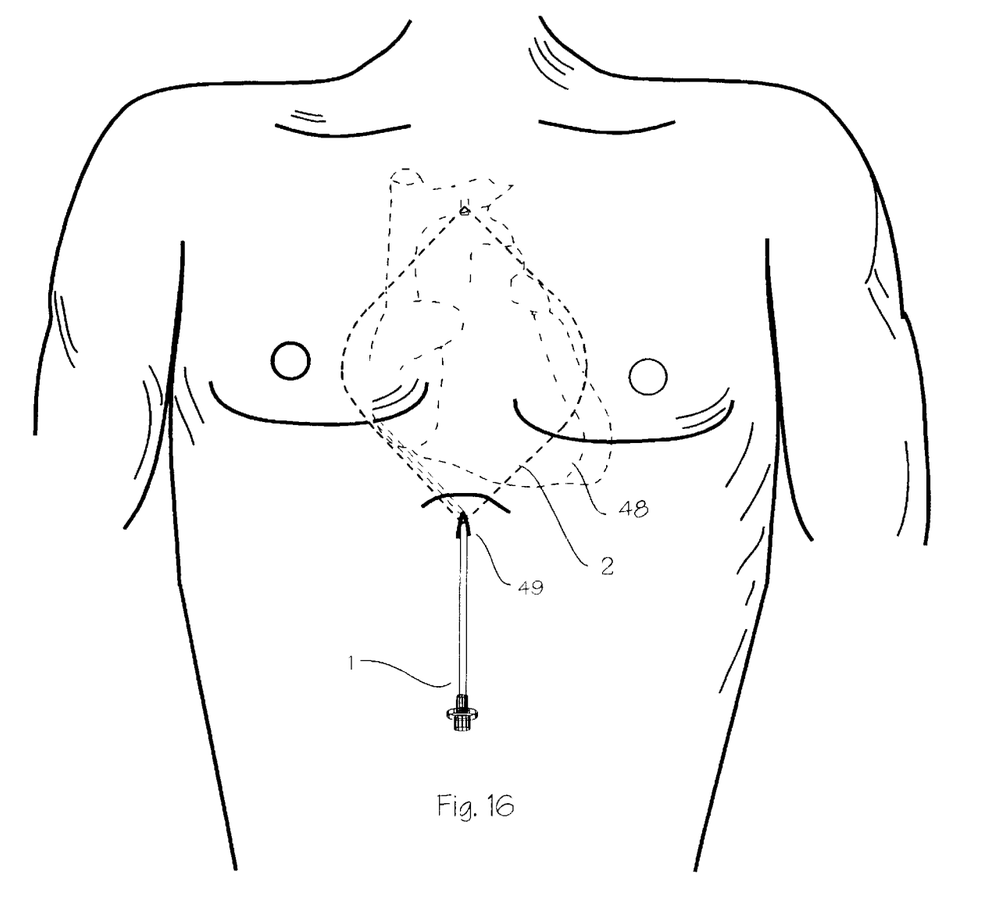
FIG. 16 shows an anterior view of the human chest and the position of the deployed cardiac pump.

When in place, the balloon portion 2 of the cardiac pump is inflated, as illustrated in FIG. 14. The balloon expands within the chest, against the sternum 44 above and the heart 48 below. The sternum provides a rigid and immovable support for the balloon, so that the balloon expands toward the heart and squeezes and compresses the heart. The heart is confined on the posterior side by the aorta, spinal column and other structures. Compression of the heart causes the heart to pump blood, as in the normal systole. After inflation has compressed the heart, the balloon is deflated and the heart relaxes and expands, just as it does in the normal diastole and draws blood from the pulmonary vein (not shown) as it does during normal operation. Upon deflation, the rounded corners 20 of the balloon will remain in place over the heart, as shown in the deflated position illustrated in FIG. 15. The anterior view of the balloon, corresponding to the FIGS. 14 and 15, is shown in FIG. 16. The balloon 2 substantially covers the heart 48 in the anterior view.

The insertion point for the balloon, just below the point of the xiphoid process, is preferred because, as illustrated, the pathway into the sternocostal space leads directly over the heart without encountering any other significant organs. Thus the danger of damage to other organs, such as the lungs, aorta, spinal column, etc., is minimized. If required, the device can be inserted through an incision in the intercostal spaces (spaces between the ribs) 55 or even from an incision near the jugular notch 56 or clavicular notch 57 at the top of the sternum, indicated in FIG. 11. Insertion through these alternative pathways will require sliding the cardiac pump near the lungs or brachio-cephalic vessels, and extra care must be exercised to avoid damage to these structures.

The method of implanting the cardiac pump described above does not require disruption or gross invasion of the rib cage which is required for open heart massage. There is no need to cut the bone or cartilage of the rib cage, and no need to retract the rib cage into an open position to gain access to the heart. This permits direct cardiac massage immediately upon cardiac arrest. The device can be inserted in non-sterile environments by paramedics as soon as they reach a cardiac arrest victim. If a cardiac arrest victim has recently undergone open chest surgery, use of the device allows direct cardiac massage without the need to disrupt the recently closed rib cage, and eliminates the danger of closed chest compression on the healing rib cage. It may even prove beneficial to implant the cardiac pump immediately after open chest surgery for patients at high risk of perioperative cardiac arrest (thus the utility of an embodiment constructed without the rigid tube which facilitates insertion). In this case, the balloon may be secured in place with resorbable sutures, suturing the balloon to the anterior chest wall or rib cage.

Figure 17:
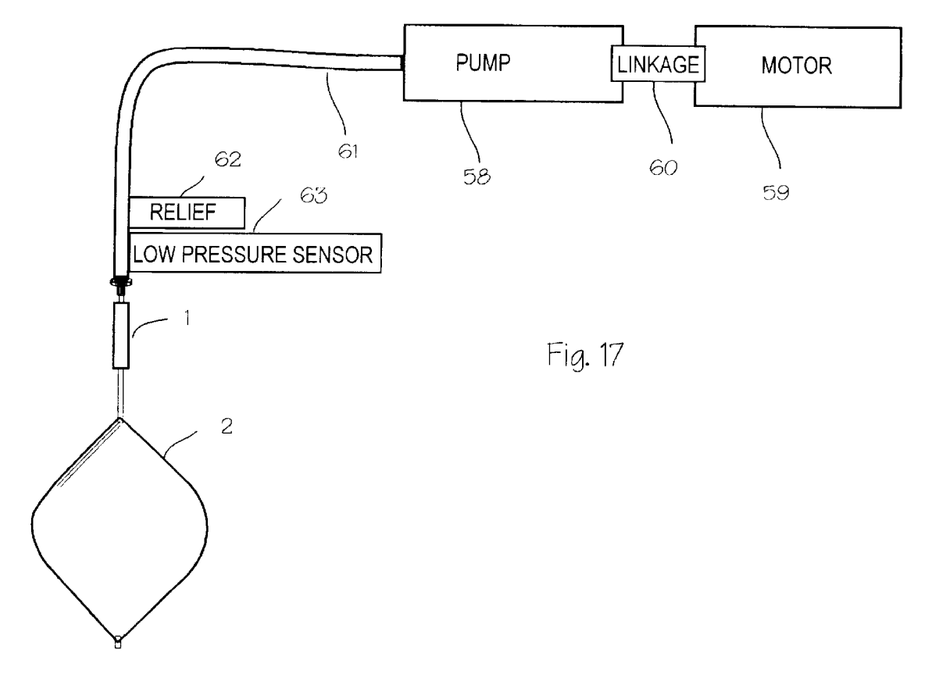
FIG. 17 is a schematic of a-manual pumping mechanism for the cardiac pump.

The mechanism for continuously inflating and deflating the cardiac pump may be provided in a variety of embodiments. Shown in FIG. 17 is one such system, comprised of a standard dual acting pump 58 such as the Guzzler™ 1.5 inch hand pump available from The Bosworth Company of East Providence, R.I. The pump is hand operated, and may also be operated by motor 59 through releasable linkage or clutch 60. On each down-stroke, a certain amount of air is forced into the cardiac pump balloon 2, and on each up-stroke, the air is drawn from the cardiac pump balloon. The specifications for the exact amount or air should be chosen to avoid the possibility of bursting the balloon and also to ensure adequate inflation pressure for compressing the heart. The positive displacement pump with an output matched to the volume of the expanded balloon is preferred. The air pump 58 is attached to the cardiac pump 1 through a supply line 61 of tygon tubing or other flexible tubing hooked up to the connector 13 on the cardiac pump 1. A pressure relief valve 62 can be provided on the supply line, or at any convenient point in the system. A low pressure warning sensor can be provided in the supply line or at any convenient point in the system, its purpose being to indicate a low pressure condition which would indicate the balloon has ruptured or that the air supply line to the cardiac pump is leaking (and, consequently, the cardiac pump is not inflating to compress the heart and provide the needed cardiac massage). The pump handle may be attached to the small electric motor and operated automatically, rather than manually, thus eliminating the fatigue of extended operation by hand. The motor is operated by battery or household current adapter or power supplies available in ambulances. In case of failure of the electric motor, the pump handle may be uncoupled from the motor allowing the pump to be operated by hand.

Use of an automatic inflation system is preferred in order to provide consistent cardiac massage over an extended period of time. The speed of the pump can be adjusted to achieve the desired pace of compressions per minute. Currently, it is standard to provide 80 compressions per minute, but some studies indicate that 120 compressions per minute in a technique called high impulse CPR and active compression/decompression may be better. An adjustable rate of compression will provide for optimization of the compression rate. The amount of air provided in each stroke may be set by choosing a positive displacement pump with an appropriate output volume or by regulating the pressure output of the pump. The stroke of the pump or the pressure limit may be adjusted to achieve optimal compression. In this manner, the rate and the amount of inflation can be provided more consistently with the cardiac pump when operated by motor than when operated by hand, and the problem of operator fatigue is eliminated.

Inflation air may be provided by other means, such as a centrifugal air pump or compressor or compressed air tank. Where continuous air supply is used, such as with a centrifugal air pump, the cycling of the cardiac pump may be accomplished by venting air from the supply line and the balloon at regular intervals, thus allowing the natural resiliency of the thoracic cavity and the heart to act upon the unpressurized balloon to deflate the balloon and allow the heart to expand and take in blood from the lungs. The high-pressure source used to inflate the balloon can also, through the use of a Venturi vacuum generator, be used to actively deflate the balloon. For active deflation of the balloon while using a high-pressure gas source, the pressurized air used to fill the balloon can be alternately bypassed (using a three way valve) to a Venturi vacuum pump which draws suction on the balloon. The alternate cycling can be accomplished with a solenoid operated valve, a pneumatically operated valve, or manually, with appropriate valve configurations for aligning gas flow for inflating and deflating the balloon. While air has been suggested as the preferred inflation fluid, water, saline solution, $CO_2$, inert gases, etc., may be substituted as the inflation fluid.

It will at times be desirable to provide for defibrillation of a heart attack victim while the balloon is in place. This may happen, for example, when a heartbeat is restored with treatment after a period of cardiac massage but fibrillation occurs for which the indicated treatment is electrical cardioversion rather than cardiac massage. Thus a balloon that is combined with defibrillation electrodes is desirable. To accomplish this, the cardiac pump which is fitted with several patch electrodes on the posterior surface of the balloon. The electrodes are connected to a standard defibrillator power source through insulated electrical wires which are potted to the electrodes with a flexible electrical epoxy and passed through cable sheath attached to the insertion rod.

When the balloon is in place within the patient, in the anterior mediastinum, the posterior surface with the electrodes will face the heart, and be in contact with the anterior surface of the pericardium. Electrical activity of the heart can be monitored through the pericardium, and the electrical stimulus required for cardioversion can be applied through the pericardium. The electrodes may be used as dual purpose sensing electrodes and electrical stimulus electrodes, or they may be provided as a pair of sensing electrodes and a pair of cardioversion electrodes. The electrodes may be used as monopolar electrodes or bipolar electrodes, as medically indicated. The electrodes are made of standard material for patch electrodes and surface electrodes, and may also be made of simple electrically conductive sheaths of, for example, copper or other metal or electrically conductive polymers. The electrodes are attached to the balloon with flexible adhesive. The electrical wires are secured to the balloon with adhesive or an overlying layer of balloon material heat sealed to the balloon over the wires.

A sensing circuit may be included in the defibrillation power source circuitry for the purpose of monitoring the heartbeat when restored. The sensing circuit and monitor can be used to alert the medic that defibrillation has occurred. Cardioversion can be accomplished automatically upon sensing fibrillation of absence of heartbeat, as is done with pacemakers, or may be accomplished manually through the balloon mounted electrodes. The sensor and alarm circuitry may be interconnected with the air pump control circuitry in order to stop the cardiac pump during defibrillation. The air pump may be stopped with the balloon inflated or deflated to ensure optimum contact with the pericardium during delivery of electrical stimulus through the electrodes.

All of the component parts of the device can fit into a kit the size of a brief case or suit case, and can be made readily transportable for use in any environment. In an embodiment intended for paramedic and ambulance use, it is expected that the motor, pump and an electric battery will be provided in single case which also holds several cardiac massage balloon assemblies and several lengths of supply line to permit use in any situation. In an embodiment intended for use in hospitals and emergency rooms, the components of the entire system may be provided in a rolling cart, and may be included in crash carts.

The repeated inflation and deflation of the cardiac pump can be continued indefinitely, and can be stopped when the cardiac arrest victim is resuscitated and recovers a normal heartbeat, or until the victim is ready for reparative surgery, such as a coronary bypass, pacemaker implantation or other surgery, or until it is determined that the victim cannot be revived. If the victim recovers a heartbeat spontaneously while the cardiac pump is operating, the pump may be stopped and the balloon deflated. This will allow the heart to beat without substantial interference from the balloon, but will leave the balloon in place in case the victim's heart stops beating again. When the balloon must be removed, it is deflated and pulled out of the chest, and the flexibility of the balloon will allow easy removal through the small incision used for insertion. As part of the recovery process, the small incision in the skin and the small puncture in the diaphragm may be closed with sutures or staples.

One way in which the use of the cardiac pump may be optimized is to use it in conjunction with a $CO_2$ monitor placed in the victims airway. The $CO_2$ content of the exhalant during CPR indicates the success of the resuscitation effort, according to Gudipati, et al., Expired Carbon Dioxide: A Non-Invasive Monitor Of Cardiopulmonary Resuscitation, 77 Circulation 234 (1988). By measuring the $CO_2$ in the expired air, medics can determine whether or not the cardiac pump is performing adequately. If expired $CO_2$ measurements indicate that blood flow is insufficient, the volume and/or pressure of air injected into the cardiac pump balloon may be increased to cause more rapid expansion and larger expansion, or the pace of inflation and deflation may be adjusted within the medically accepted ranges (currently 80–120 compressions per minute).

A wide variety of materials and components may be used to construct the cardiac massage balloon and the manual and motorized inflation systems described above. The materials and specific components mentioned in connection with the devices have proven suitable for experimental use. It is specifically intended that balloon materials and configurations may be optimized upon further development and experience with the cardiac massage pump. Thus, while the preferred embodiments of the devices and methods have been described, they are merely illustrative of the principles of the invention. Other embodiments and configurations may be devised without departing from the spirit of the inventions and the scope of the appended claims.

We claim:

1. A minimally invasive device for cardiac massage within the chest of a human, said device comprising:
   a rigid insertion rod having a distal end and a proximal end, and having a fluid conduit communicating from the proximal end to the distal end, and having an fluid port in the distal end and a fluid port in the proximal end, said distal and proximal fluid ports communicating with the fluid conduit so that the fluid ports and fluid conduit provide a pathway for fluid to pass through the rigid tube;

a balloon mounted on the distal end of the rigid insertion rod over the distal fluid port so that the balloon may be inflated and deflated by passage of fluid through the fluid conduit, said balloon and distal end of the rod forming an insertion portion;

said insertion portion being sized and dimensioned to enable insertion of the insertion portion within the chest of the human between the heart and the sternum of the human, when the balloon is deflated;

said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and an introducer sleeve adapted to surround the balloon and insertion portion when the balloon is in the compact configuration, said introducer sleeve having a score line along its length to permit it to be torn off the insertion rod after the insertion rod is inserted into the chest, said score line being disposed laterally on the introducer sleeve.

2. A minimally invasive device for cardiac massage within the chest of a human, said device comprising:

a rigid insertion rod having a distal end and a proximal end, and having a fluid conduit communicating from the proximal end to the distal end, and having an fluid port in the distal end and a fluid port in the proximal end, said distal and proximal fluid ports communicating with the fluid conduit so that the fluid ports and fluid conduit provide a pathway for fluid to pass through the rigid tube;

a balloon mounted on the distal end of the rigid insertion rod over the distal fluid port so that the balloon may be inflated and deflated by passage of fluid through the fluid conduit, said balloon and distal end of the rod forming an insertion portion;

said insertion portion being sized and dimensioned to enable insertion of the insertion portion within the chest of the human between the heart and the sternum of the human, when the balloon is deflated;

said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and an introducer sleeve adapted to surround the balloon and insertion portion when the balloon is in the compact configuration; and a pull tab disposed on the proximal end of the introducer sleeve, said pull tab disposed on the introducer sleeve so as to indicate the proper orientation of the device in relationship to the chest of the patient.

3. A minimally invasive device for cardiac massage within the chest of a human, said device comprising:

a rigid insertion rod having a distal end and a proximal end, and having a fluid conduit communicating from the proximal end to the distal end, and having an fluid port in the distal end and a fluid port in the proximal end, said distal and proximal fluid ports communicating with the fluid conduit so that the fluid ports and fluid conduit provide a pathway for fluid to pass through the rigid tube;

a balloon mounted on the distal end of the rigid insertion rod over the distal fluid port so that the balloon may be inflated and deflated by passage of fluid through the fluid conduit, said balloon and distal end of the rod forming an insertion portion;

said insertion portion being sized and dimensioned to enable insertion of the insertion portion within the chest of the human between the heart and the sternum of the human, when the balloon is deflated;

said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and an introducer sleeve adapted to surround the balloon and insertion portion when the balloon is in the compact configuration; and a pull tab disposed on the proximal end of the introducer sleeve, said pull tab disposed on the introducer sleeve a predetermined distance from the distal end of the insertion rod, said pull tab being sized and dimensioned to limit insertion of the device into the body to the predetermined distance.

4. A minimally invasive device for cardiac massage within the chest of a human, said device comprising:

a rigid insertion rod having a distal end and a proximal end, and having a fluid conduit communicating from the proximal end to the distal end, and having an fluid port in the distal end and a fluid port in the proximal end, said distal and proximal fluid ports communicating with the fluid conduit so that the fluid ports and fluid conduit provide a pathway for fluid to pass through the rigid tube;

a balloon mounted on the distal end of the rigid insertion rod over the distal fluid port so that the balloon may be inflated and deflated by passage of fluid through the fluid conduit, said balloon and distal end of the rod forming an insertion portion;

said insertion portion being sized and dimensioned to enable insertion of the insertion portion within the chest of the human between the heart and the sternum of the human, when the balloon is deflated;

said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and an introducer sleeve adapted to surround the balloon and insertion portion when the balloon is in the compact configuration; and a stop disposed on the proximal end of the introducer sleeve, said stop disposed on the introducer sleeve a predetermined distance from the distal end of the insertion rod, said stop being sized and dimensioned to limit insertion of the device into the body to the predetermined distance.

5. A method of placing a balloon within the thoracic cavity of a human and compressing the heart of the patient, said method comprising:

provicing a balloon device for cardiac massage within the chest of a human, said device comprising:
- a rigid insertion rod having a distal end and a proximal end, said rigid insertion rod having a fluid conduit communicating from the proximal end to the distal end thereof, and having a fluid port in the distal end and a fluid port in the proximal end, said distal and proximal fluid ports communicating with the fluid conduit so that the fluid ports and fluid conduits provide a pathway for fluid to pass through the rigid tube;
- a balloon mounted on a the distal end of the rigid insertion rod over the distal fluid port so that the balloon may be inflated and deflated by passage of fluid through the fluid conduit, said balloon and distal end of the rod forming an insertion portion;
- said insertion portion being sized and dimensioned to enable insertion of the insertion portion within the chest of the human between the heart and the sternum of the human, when the balloon is deflated;
- said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and
- an introducer sleeve adapted to surround the balloon and insertion portion when the balloon is in the compact configuration, said introducer sleeve having a score line along its length to permit it to be torn off the insertion rod after the insertion rod is inserted into the chest, said score line being disposed laterally on the introducer sleeve; and inserting the insertion portion of the balloon device into the thoracic cavity of the human, so that the balloon is situated between the heart and the sternum;

pulling the introducer sleeve proximally and laterally out of the chest, while holding the insertion portion of the device in place inside the chest, thereby removing the introducer sleeve from the balloon without imparting substantial anteriorly or posteriorly directed force on the device; and alternately inflating and deflating the balloon to cause repeated compression of the heart.

6. A method of placing a balloon within the thoracic cavity of a human and compressing the heart of the patient, said method comprising:

providing a balloon device for cardiac massage within the chest of a human, said device comprising:
- a rigid insertion rod having a distal end and a proximal end, said rigid insertion rod having a fluid conduit communicating from the proximal end to the distal end thereof, and having a fluid port in the distal end and a fluid port in the proximal end, said distal and proximal fluid ports communicating with the fluid conduit so that the fluid ports and fluid conduits provide a pathway for fluid to pass through the rigid tube;
- a balloon mounted on a the distal end of the rigid insertion rod over the distal fluid port so that the balloon may be inflated and deflated by passage of fluid through the fluid conduit, said balloon and distal end of the rod forming an insertion portion;
- said insertion portion being sized and dimensioned to enable insertion of the insertion portion within the chest of the human between the heart and the sternum of the human, when the balloon is deflated;
- said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and
- an introducer sleeve adapted to surround the balloon and insertion portion when the balloon is in the compact configuration; and
- a pull tab disposed on the proximal end of the introducer sleeve, said pull tab disposed on the introducer sleeve so as to indicate the proper orientation of the device in relationship to the chest of the patient;

inserting the insertion portion of the balloon device into the thoracic cavity of the human while maintaining the pull tab in a predetermined orientation with the thoracic cavity, so that the balloon is situated between the heart and the sternum;

pulling the pull tab proximally in order to pull the introducer sleeve out of the chest, while holding the insertion portion of the device in place inside the chest, thereby removing the introducer sleeve from the balloon; and alternately inflating and deflating the balloon to cause repeated compression of the heart.

7. A method of placing a balloon within the thoracic cavity of a human and compressing the heart of the patient, said method comprising:

providing a balloon device for cardiac massage within the chest of a human, said device comprising:
- a rigid insertion rod having a distal end and a proximal end, said rigid insertion rod having a fluid conduit communicating from the proximal end to the distal end thereof, and having a fluid port in the distal end and a fluid port in the proximal end, said distal and proximal fluid ports communicating with the fluid conduit so that the fluid ports and fluid conduits provide a pathway for fluid to pass through the rigid tube;
- a balloon mounted on a the distal end of the rigid insertion rod over the distal fluid port so that the balloon may be inflated and deflated by passage of fluid through the fluid conduit, said balloon and distal end of the rod forming an insertion portion;
- said insertion portion being sized and dimensioned to enable insertion of the insertion portion within the chest of the human between the heart and the sternum of the human, when the balloon is deflated;
- said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and
- an introducer sleeve adapted to surround the balloon and insertion portion when the balloon is in the compact configuration; and
- a pull tab disposed on the proximal end of the introducer sleeve, said pull tab disposed on the introducer sleeve a predetermined distance from the distal end of the insertion rod, said pull tab being sized and dimensioned to limit insertion of the device into the body to the predetermined distance;

inserting the insertion portion of the balloon device into the thoracic cavity of the human until the pull tab meets the body, so that the balloon is situated between the heart and the sternum and further insertion is impeded by the pull tab;

pulling the pull tab proximally in order to pull the introducer sleeve out of the chest, while holding the insertion portion of the device in place inside the chest, thereby removing the introducer sleeve from the balloon; and alternately inflating and deflating the balloon to cause repeated compression of the heart.

8. A method of placing a balloon within the thoracic cavity of a human and compressing the heart of the patient, said method comprising:

provid­ing a balloon device for cardiac massage within the chest of a human, said device comprising:

a rigid insertion rod having a distal end and a proximal end, said rigid insertion rod having a fluid conduit communicating from the proximal end to the distal end thereof, and having a fluid port in the distal end and a fluid port in the proximal end, said distal and proximal fluid ports communicating with the fluid conduit so that the fluid ports and fluid conduits provide a pathway for fluid to pass through the rigid tube;

a balloon mounted on a the distal end of the rigid insertion rod over the distal fluid port so that the balloon may be inflated and deflated by passage of fluid through the fluid conduit, said balloon and distal end of the rod forming an insertion portion;

said insertion portion being sized and dimensioned to enable insertion of the insertion portion within the chest of the human between the heart and the sternum of the human, when the balloon is deflated;

said balloon adapted to assume an inflated state wherein the balloon has a configuration sized and dimensioned to compress the heart when said balloon is inflated within the chest of the human and a deflated state in which it may be compacted into a compact configuration in close proximity to the insertion rod when deflated; and an introducer sleeve adapted to surround the balloon and insertion portion when the balloon is in the compact configuration; and a stop disposed on the proximal end of the introducer sleeve, said stop disposed on the introducer sleeve a predetermined distance from the distal end of the insertion rod, said stop being sized and dimensioned to limit insertion of the device into the body to the predetermined distance;

inserting the insertion portion of the balloon device into the thoracic cavity of the human until the stop meets the body, so that the balloon is situated between the heart and the sternum and further insertion is impeded by the stop;

pulling the introducer sleeve out of the chest, while holding the insertion portion of the device in place inside the chest, thereby removing the introducer sleeve from the balloon; and alternately inflating and deflating the balloon to cause repeated compression of the heart.

\* \* \* \* \*